United States Patent
Pellegrini et al.

(10) Patent No.: US 8,168,446 B2
(45) Date of Patent: *May 1, 2012

(54) MONOCLONAL AND POLYCLONAL ANTIBODIES TO EQUINE ALBUMIN AND HEMOGLOBIN AND APPARATUS AND METHODS USING THE ANTIBODIES IN THE IDENTIFICATION AND LOCALIZATION OF ULCERS AND OTHER DIGESTIVE TRACT BLEEDING IN EQUINES

(75) Inventors: Franklin L. Pellegrini, Streetsboro, OH (US); Scott D. Carter, Macedonia, OH (US)

(73) Assignee: Freedom Health, LLC, Aurora, OH (US)

( * ) Notice: Subject to any disclaimer, the term of this patent is extended or adjusted under 35 U.S.C. 154(b) by 282 days.

This patent is subject to a terminal disclaimer.

(21) Appl. No.: 12/619,459

(22) Filed: Nov. 16, 2009

(65) Prior Publication Data

US 2010/0062458 A1    Mar. 11, 2010

Related U.S. Application Data

(60) Division of application No. 11/563,998, filed on Nov. 28, 2006, now Pat. No. 7,629,180, which is a continuation-in-part of application No. 11/291,696, filed on Dec. 1, 2005, now abandoned.

(60) Provisional application No. 60/633,167, filed on Dec. 4, 2004.

(51) Int. Cl.
*G01N 33/53* (2006.01)

(52) U.S. Cl. .......... 436/518; 436/514; 436/63; 436/169; 436/513; 436/530; 436/805; 436/810; 435/7.21; 435/7.92; 435/7.94; 435/287.1; 435/287.2; 435/287.7; 435/805; 435/810; 435/970; 422/430

(58) Field of Classification Search .................. 436/514, 436/518, 63, 169, 513, 530, 805, 810; 435/7.21, 435/7.92, 7.94, 287.1, 287.2, 287.7, 805, 435/810, 970; 422/430; 7/514, 518, 63, 7/169, 513, 530, 805, 810
See application file for complete search history.

(56) References Cited

U.S. PATENT DOCUMENTS 4,260,393 A    4/1981    Gibson
(Continued)

FOREIGN PATENT DOCUMENTS

EP    0070366    1/1983
(Continued)

OTHER PUBLICATIONS

Zhang Ya-Li et al: "Early diagnosis for colorectal cancer in China." Feb. 2002, World Journal of Gastroenterology: WJG Feb. 2002, vol. 8, Nr. 1, pp. 21-25, XP008086174 ISSN: 1007-9327 *abstract*.

(Continued)

*Primary Examiner* — Bao Thuy L Nguyen
(74) *Attorney, Agent, or Firm* — Reinhart Boerner Van Deuren s. c.

(57) ABSTRACT

A diagnostic and testing apparatus and related methods for the use of the same are disclosed which derive and use antibodies to equine albumin and equine hemoglobin in testing apparatus, kits, and methods for detecting and localizing gastric and colonic ulcers or bleeding in horses. Fecal droppings from a horse to be tested are placed in a container together with a buffered liquid solution and mixed thoroughly, following which several drops of liquid from the container are placed into a test kit. Visual markers in the test kits signify the detection of the indicators equine hemoglobin and equine albumin, which are respectively indicative of the presence of gastric and/or colonic ulcers or bleeding.

22 Claims, 3 Drawing Sheets

U.S. PATENT DOCUMENTS

| | | | |
|---|---|---|---|
| 4,675,160 | A | 6/1987 | Talmage et al. |
| 4,806,468 | A | 2/1989 | Wagner et al. |
| 5,064,766 | A | 11/1991 | Wardlaw et al. |
| 5,081,040 | A | 1/1992 | Patel et al. |
| 5,094,956 | A | 3/1992 | Grow et al. |
| 5,141,850 | A | 8/1992 | Cole et al. |
| 5,198,365 | A | 3/1993 | Grow et al. |
| 5,460,969 | A | 10/1995 | Fielder et al. |
| 5,552,295 | A | 9/1996 | Stanker et al. |
| 5,712,170 | A | 1/1998 | Kouvonen et al. |
| 6,319,676 | B1 | 11/2001 | Nazareth et al. |
| 6,767,714 | B2 | 7/2004 | Nazareth et al. |
| 6,844,195 | B2 | 1/2005 | Craine |
| 7,067,264 | B2 | 6/2006 | Bagaria |
| 2002/0076820 | A1 | 6/2002 | Craine |
| 2003/0180826 | A1 | 9/2003 | Chang et al. |
| 2004/0033623 | A1 | 2/2004 | Shag et al. |
| 2004/0096988 | A1 | 5/2004 | Kang et al. |
| 2004/0219620 | A1 | 11/2004 | Mayer |
| 2004/0241776 | A1 | 12/2004 | Geister et al. |
| 2006/0134707 | A1 | 6/2006 | Pellegrini |

FOREIGN PATENT DOCUMENTS

| | | |
|---|---|---|
| GB | 2204398 | 11/1988 |
| WO | 9422017 | 9/1994 |
| WO | 0029852 | 5/2000 |
| WO | 0244738 | 6/2002 |
| WO | 2006062800 | 6/2006 |

OTHER PUBLICATIONS

Sieg A et al: "Screening for colorectal neoplasms with a new immunological human faecal haemoglobin and albumin test." European Journal of Cancer Prevention: The Official Journal of the European Cancer Prevention Organisation (ECP) Aug. 1998, vol. 7, No. 4, Aug. 1998, pp. 279-285, XP008086175 ISSN: 0959-8278.

Sieg A et al: "Validity of new immunological human fecal hemoglobin and albumin tests in detecting colorectal neoplasms—an endoscopy-controlled study." Zeitschrift Fur Gastroenterologie Jun. 1998, vol. 35, No. 6, Jun. 1998, pp. 485-490, XP008086220 ISSN: 0044-2771 *abstract; tables 1-4*.

Uda Taizo et al. "Production of Immunological Characterization for Anti Hemin Monoclonal Antibody." The Chemical Society of Japan, Chemistry Letters, 1993, pp. 1923-1926.

Takahashi Mizuke et al. "Design of Novel Porphyrin-Binding Peptides Based on Antibody CDR." Bioorganic and Medicinal Chemistry Letters, vol. 8, No. 15, Aug. 4, 1998, pp. 2023-2026.

O'Connor, Michael S. et al. "Evaluation of Urine Sucrose Concentration for Detection of Gastric Ulcers in Horses." American Journal of Veterinary Research, vol. 65, No. 1, Jan. 2004, pp. 31-39.

McClure Scott R. et al. "Prevalence of Gastric Ulcers in Show Horses." Journal of the American Veterinary Medical Association, vol. 215, No. 8, Oct. 15, 1999, pp. 1130-1133.

|  | NO ALBUMEN | ALBUMEN PRESENT |
|---|---|---|
| NO HEMOGLOBIN | ULCERS NOT PRESENT | COLONIC ULCERS DETECTED |
| HEMOGLOBIN PRESENT | GASTRIC ULCERS DETECTED | COLONIC ULCERS OR BOTH GASTRIC AND COLONIC ULCERS DETECTED |

FIG. 4

MONOCLONAL AND POLYCLONAL ANTIBODIES TO EQUINE ALBUMIN AND HEMOGLOBIN AND APPARATUS AND METHODS USING THE ANTIBODIES IN THE IDENTIFICATION AND LOCALIZATION OF ULCERS AND OTHER DIGESTIVE TRACT BLEEDING IN EQUINES

IDENTIFICATION OF RELATED APPLICATIONS

This patent application is a divisional of U.S. patent application Ser. No. 11/563,998, filed on Nov. 28, 2006, now U.S. Pat. No. 7,629,180 entitled "Test Kit for the Rapid Detection and Localization of Digestive Tract Bleeding in Equines," which patent application is assigned to the assignee of the present invention, and which patent application is a continuation-in-part of U.S. patent application Ser. No. 11/291,696, filed on Dec. 1, 2005, now abandoned entitled "Monoclonal and Polyclonal Antibodies to Equine Hemoglobin and Apparatus and Methods Using the Antibodies and/or Peroxidase Reactions in the Identification and Localization of Ulcers in Equines," which patent application is assigned to the assignee of the present invention, and which patent application claimed priority of U.S. Provisional Patent Application No. 60/633,167, which is entitled "Antibodies to Equine Globin and Equine Hematin and Apparatus and Methods Using the Antibodies in the Identification and Localization of Ulcers in Equines," and which was filed on Dec. 4, 2004, all of which patent applications are hereby incorporated herein by reference in their entirety.

BACKGROUND OF THE INVENTION

Field of the Invention

The present invention relates generally to diagnostic and testing apparatus and methods, and more particularly to antibodies to equine hemoglobin and equine albumin and the use thereof in testing apparatus, kits, and methods for detecting and localizing gastric and colonic ulcers and other digestive tract bleeding in horses.

Prior to discussing the testing for and the diagnosis of ulcers in horses, it is beneficial to discuss the somewhat unique digestive tract anatomy of horses which contributes to a high incidence of digestive tract ulcers in horses. In the case of humans and most other animals, gastric acid is secreted in the stomach in response to eating. In contrast, horses have developed over millennia as trickle feeders (eating slowly but more or less continuously over most of the day), and their digestive systems are geared for such a diet, with a continuous production of gastric juices and bile secretion into the foregut from the liver. Thus, the stomach of a horse may be thought of as an acid pump that produces gastric acid more or less continuously through the day, whether or not the horse is being fed.

As a consequence of their anatomy and modern feeding and care practices, all horses, and particularly performance horses, have a very high incidence of gastric (stomach) ulcers. In racehorses, for example, as much as ninety-seven percent of the racehorse population has been reported to have digestive tract ulcers, with the percentage of show horses having digestive tract ulcers lagging only slightly behind. Even performance horse foals have been inflicted with this condition, with approximately sixty percent of performance horse foals having digestive tract ulcers. While pleasure horses have a lower incidence of digestive tract ulcers than show horses, the increasing incidence of digestive tract ulcers in the last two decades has been significant for all segments of the horse population, including pleasure horses.

While incidences of colonic ulcers (ulcers in the cecum and/or colon of the horse) have been largely unexplored, they may also represent a different and equally severe health issue for horses. One of the only scientific studies to date looked specifically at the incidence of colonic ulcers and showed surprising results. In this study, a random cross-section of horses had an approximately fifty-five percent incidence of gastric ulcers and a forty percent incidence of colonic ulcers. The incidences of gastric and colonic ulcers were not identical, meaning that some horses had only gastric ulcers and other horses had only colonic ulcers. However, a large percentage of the horses that had colonic ulcers also had gastric ulcers, with less than thirty percent of the horse population as a whole not having either gastric or colonic ulcers. As mentioned above, the incidence of digestive tract ulcers for show horses and racehorses is even higher than these statistics for the general horse population.

There are a number of solutions to the problem of digestive tract ulcers in horses that have been utilized in the art. Such solutions have included the use of antacids to temporarily neutralize acid in the stomach, the use of drugs to inhibit the production of gastric acid, and extended rest and a diet of forage. More recently, a novel and highly effective dietary supplement has been developed to treat and/or prevent gastric ulcers and colonic ulcers, as disclosed in U.S. patent application Ser. No. 10/435,367, filed on May 9, 2003, entitled "Dietary Supplement and Method for the Treatment and Prevention of Digestive Tract Ulcers in Equines and Other Animals," which patent application is assigned to the assignee of the present invention, and which patent application is hereby incorporated herein by reference in its entirety.

While such treatments are available, it has remained extremely difficult to diagnose gastric ulcers in horses with a high degree of precision, and it has not been possible to diagnose colonic ulcers in horses at all. The most commonly utilized method of diagnosing equine ulcers, namely the use of symptoms (which are frequently vague, non specific signs such as weight loss, poor appetite, lethargy, or intermittent fever) combined with the perceived results of treatment, has been found to be nearly completely unreliable. This is due to the fact that there can be many potential causes of the same symptoms, and not all horses show the same or even marked symptoms of ulceration. As such, the use of this technique is often little better than a guessing game.

The only reliable way of diagnosing gastric ulcers in horses has been through the use of a three meter video endoscope, which has the significant disadvantages of being expensive, time-consuming, and stressful (both to the horse and to the trainer/owner). The cost to purchase a three meter video endoscope is quite high, and is prohibitively expensive to owners and all but the most elite of trainers. On top of the cost of the endoscope is the fact that the procedure is both cumbersome and time-consuming. Owners, trainers, and veterinarians who do not have a three meter video endoscope must consult a clinic or a veterinarian who has an endoscope. This takes additional time and expense, is even more stressful to the horse, and is frustrating since it takes the care of the horse out of the hands of the owner, trainer, or usual veterinarian.

In addition, even if a three meter video endoscope is available and is used, the results are restricted to what is viewable by the device, namely the stomach tissues. While such a device is effective at viewing and diagnosing stomach ulcers, diagnosis of ulceration in the remaining ninety-five percent of a horse's digestive tract is still impossible with this device. The hindgut (approximately seventy-five feet of the small intestine, cecum, and colon) cannot be viewed using an endoscope since endoscopes of sufficient length are not available and since the use of an endoscope would require emptying the hindgut sufficiently that it would likely kill the horse. In fact, it has only been recently that the high incidence of colonic ulcers in horses has been documented, and that was done solely through the use of post-mortem visual analysis.

It is accordingly the primary objective of the present invention that it present an equine ulcer and digestive tract bleeding test kit and a related method for the use of the test kit which are efficacious in the diagnosis of both gastric ulcers or bleeding and colonic ulcers or bleeding in horses. It is a related objective of the present invention that it provide a highly specific indication as to the presence of either gastric ulcers or bleeding or colonic ulcers or bleeding, or both. It is another related objective of the present invention that it be highly reliable both in its identification of the existence of ulcers or bleeding in a horse as well as its identification of the type(s) of the ulcers which are present in the horse, and that it not produce excessive false positive readings.

It is another objective of the present invention that the test be both simple and quick to perform, and that it require no special skill or training in order for a user to perform the test. It is a further objective of the present invention that it be entirely self-contained, requiring no laboratory analysis or additional processing equipment so that it can be performed anywhere as a field test. It is still another objective of the present invention that it provide the results of the test quickly, in minutes rather than requiring an extended time.

The equine ulcer or bleeding test kit of the present invention must also be of construction which is both durable and long lasting, and it should also not require special storage conditions for the test kits in order to ensure that they have an extended shelf life. In order to enhance the market appeal of the equine ulcer or bleeding test kit of the present invention, it should also be of inexpensive construction to thereby afford it the broadest possible market. Finally, it is also an objective that all of the aforesaid advantages and objectives of the equine ulcer or bleeding test kit and method of the present invention be achieved without incurring any substantial relative disadvantage.

SUMMARY OF THE INVENTION

The disadvantages and limitations of the background art discussed above are overcome by the present invention. With this invention, an equine ulcer and digestive tract bleeding test kit and a method of using the test kit are provided which are able to provide a highly sensitive and specific identification of the presence of either or both of gastric and colonic ulcers and other digestive tract bleeding in horses, with the equine ulcer or bleeding test kit and method clearly distinguishing between gastric ulcers or bleeding and colonic ulcers or bleeding. The ulcer or bleeding test of the present invention is referred to as a fecal blood test, since it identifies components of blood contained in the feces of the horse being tested.

According to the teachings of the present invention, two blood components have been identified which are respectively highly indicative of the presence of a gastric ulcer or bleeding and/or a colonic ulcer or bleeding. The inventors of the present invention have determined that the presence of intact equine albumin which is contained in feces is most likely of colonic origin. This is due to the fact that equine blood albumin from a gastric ulcer (and any other blood cranial to the duodenum, for that matter) would be degraded by acids and peptidases in the stomach, making equine albumin undetectable in feces. However, equine hemoglobin contained in blood from a gastric ulcer or bleeding will survive the acids and peptidases in the stomach at least in part, making it detectable in the feces.

Thus, the presence of intact equine albumin in the feces is indicative of the existence of a colonic ulcer or bleeding, while the presence of equine hemoglobin is indicative of the existence of either a gastric ulcer or bleeding or a colonic ulcer or bleeding or both a gastric ulcer or bleeding and a colonic ulcer or bleeding. It will further be appreciated by those skilled in the art that an equine ulcer or bleeding test kit and method using as indicators equine albumin and equine hemoglobin will provide a good indicator of both the presence and the location of one or more ulcers or bleeding in the horse. The preferred form of the equine ulcer or bleeding test kit and method of the present invention is an immunoassay which is designed to detect the presence of the equine albumin and equine hemoglobin indicators, and specifically the equine ulcer or bleeding test of the preferred embodiment of the present invention is an Enzyme-Linked Immunosorbent Assay (an "ELISA" test), which is a method typically employed in biochemistry to detect whether or not a particular substance is present in a sample.

ELISA tests are rapid immunochemical tests that involve an antibody or an antigen (immunologic molecules) and an enzyme (a protein that catalyzes a biochemical reaction). An ELISA test is used to detect a substance that has antigenic properties, primarily proteins (as opposed to small molecules and ions such as glucose and potassium), such as antibodies, bacterial antigens, and hormones. A so-called "Rapid" ELISA test is a Lateral Flow Immunoassay ("LFI") test that consists of a membrane having a fluid path from one end thereof which is attached to a fluid source to the other end thereof which is attached to a fluid sink, with three discrete and separated areas along the membrane.

The first area contains a labeled antibody, which is the antibody attached to a coloring agent, such as colored latex beads or a dye or colloidal gold. The labeled antibodies move with the flow of fluid from the first area towards the second and third areas, and ultimately the fluid sink. If the substance of interest is in the fluid, it will bind to the labeled antibodies. The second area, which is typically a line extending across the membrane, contains antibodies which are attached to the membrane.

The antibodies in the second area have an affinity for (and will attract and latch onto) the substance of interest, creating a "sandwich" with the labeled antibodies and the substance of interest being bound to the antibodies in the second area, thereby creating a colored line which is a positive reading indicating the presence of the substance of interest. The more of the substance of interest contained in the fluid, the more of the labeled antibodies which will be bound with the substance of interest to the antibodies in the second area.

The third area, which is typically also a line extending across the membrane, uses a different antibody/antigen reaction that will create a colored line if the flow and volume is sufficient, regardless of the presence of the substance of interest. This acts as a control to indicate that the test system is operating properly. The third area is on the opposite side of the second area from the first area to indicate that the fluid being tested has passed across the second area, thereby indicating that the test system has been supplied with sufficient fluid being tested for the test system to work properly.

Such a test system is generically illustrated in U.S. Pat. No. 5,602,040, to May et al., which is based on two antibodies. Particles including a first group of antibodies are attached to the surface of colored latex or gold colloid particles which have been dried onto the nitrocellulose membrane at a first end thereof, and represent the first area referenced above. A second group of antibodies are attached to a nitrocellulose membrane in the form of a line, and represent the second area referenced above.

The test is performed by absorbing a liquid sample into the nitrocellulose membrane at the first end. The particles at the first area are freed by the liquid flow and the analyte to be detected binds to the antibody on said particles. At the second area, the analyte to be detected binds also to the other antibody which is present in the line, and a visible colored line is formed to show the presence of said analyte. This type of immunochromatographic test technique is based on the flow through a membrane, and may be referred to as a "lateral flow technique." U.S. Pat. No. 5,602,040 is hereby incorporated herein by reference, as is U.S. Pat. No. 5,712,170, to Kouvonen et al., which provides an excellent summary of the art in this area.

A second format exists that may be employed that uses a "competitive exclusion" technique to generate a positive or negative result. Rather than the sandwich assay described above, purified antigen (equine albumin or equine hemoglobin) is affixed to the strip, and the target antibody is contained in the mobile phase. When no target antigen is present in the tested sample, the antibody is free to move in the mobile phase and will become attached to the affixed antigen on the strip, resulting in a line on the strip. Accordingly, the presence of a line indicates a negative result.

If, on the other hand, the target antigen is present in the tested sample, then the antigen will bind to the antibody in the mobile phase, making it unavailable to bind to the test strip, which will result in no line appearing. Accordingly, the absence of a line in this test indicates a positive result. This type of competitive exclusion test technique is described used in the drug test manufactured under the trademark ONTRAK TESTCUP by Varian, Inc. and exclusively sold by Roche Diagnostics. It is described in U.S. Pat. No. 6,375,897, to Bachand, which patent is hereby incorporated herein by reference.

LFI tests are relatively inexpensive to manufacture, easy to operate, and provide rapid analyses without the need for laboratory equipment. The antibodies in LFI tests are typically obtained by inoculating an animal with the substance of interest, after which the animal produces antibodies to that substance. This biochemical relationship is thereby utilized as the mechanism to isolate and detect the substance of interest. LFI tests are both sensitive and specific, and compare well with radioimmune assay ("RIA") tests. LFI tests have the additional advantage of not needing radioisotopes or a radiation-counting apparatus.

The preferred embodiment equine ulcer or bleeding test kit of the present invention includes two test strips which are contained in either one or two plastic casings. Fecal droppings from a horse to be tested are placed in a container (which may be, for example a bucket, a pail, a plastic bag, or a cup), a solution (which may be water or water with a buffer such as salt) is added, and the mixture is swirled, stirred, or kneaded to mix it thoroughly. An applicator such as an eye dropper is used to drop several drops of liquid from the container onto the test strips in the casings.

Over a period of time which preferably ranges from approximately five minutes to approximately thirty minutes, the two test strips will provide a visual marker representing the control indicator, and, if the indicators being tested for are present, visual markers signifying the detection of those indicators which are respectively indicative of the presence of gastric ulcers or bleeding and/or colonic ulcers or bleeding. The present invention uses two indicators, one of which is indicative of the presence of a gastric ulcer or bleeding and the other of which is indicative of the presence of a colonic ulcer or bleeding.

In the preferred embodiment, the substance of interest which, when detected, will provide an indication of the presence of a colonic ulcer or bleeding is equine albumin, and the substance of interest which, when detected, will provide an indication of the presence of a gastric ulcer or bleeding or a colonic ulcer or bleeding or both gastric and colonic ulcers or bleeding is equine hemoglobin. The equine ulcer or bleeding test kit and method of the present invention thereby diagnoses gastric and/or colonic ulcers or bleeding, providing an immediate basis for treatment.

It may therefore be seen that the present invention teaches an equine ulcer and digestive tract bleeding test kit and a related method for the use of the test kit which are efficacious in the diagnosis of both gastric ulcers or bleeding and colonic ulcers or bleeding as well as other digestive tract bleeding in horses. The equine ulcer or bleeding test kit and method of the present invention provide a highly specific indication as to the presence of either gastric ulcers or bleeding or colonic ulcers or bleeding, or both. The equine ulcer or bleeding test kit and method of the present invention are highly reliable both in their identification of the existence of ulcers or bleeding in a horse as well as their identification of the type(s) of the ulcers which are present in the horse, and do not produce excessive false positive readings.

The equine ulcer or bleeding test kit and method of the present invention are both simple and quick to perform, and they require no special skill or training in order for a user to perform the test. The equine ulcer or bleeding test kit of the present invention is entirely self-contained, and requires no laboratory analysis or additional processing equipment, thereby enabling it to be performed anywhere as a field test. The equine ulcer or bleeding test kit and method of the present invention provide the results of the test quickly, in minutes rather than requiring an extended time.

The equine ulcer or bleeding test kit of the present invention is of a construction which is both durable and long lasting, and the test kits do not require special storage conditions and have an extended shelf life. The equine ulcer or bleeding test kit of the present invention is also of inexpensive construction to enhance its market appeal and to thereby afford it the broadest possible market. Finally, all of the aforesaid advantages and objectives of the equine ulcer or bleeding test kit and method of the present invention are achieved without incurring any substantial relative disadvantage.

DESCRIPTION OF THE DRAWINGS

These and other advantages of the present invention are best understood with reference to the drawings, in which:

FIG. 4 is a chart illustrating the results of the equine ulcer or bleeding test kit as indicated by the detected presence or absence of equine albumin and the detected presence or absence of equine hemoglobin.

DETAILED DESCRIPTION OF THE PREFERRED EMBODIMENT

Figure 1:
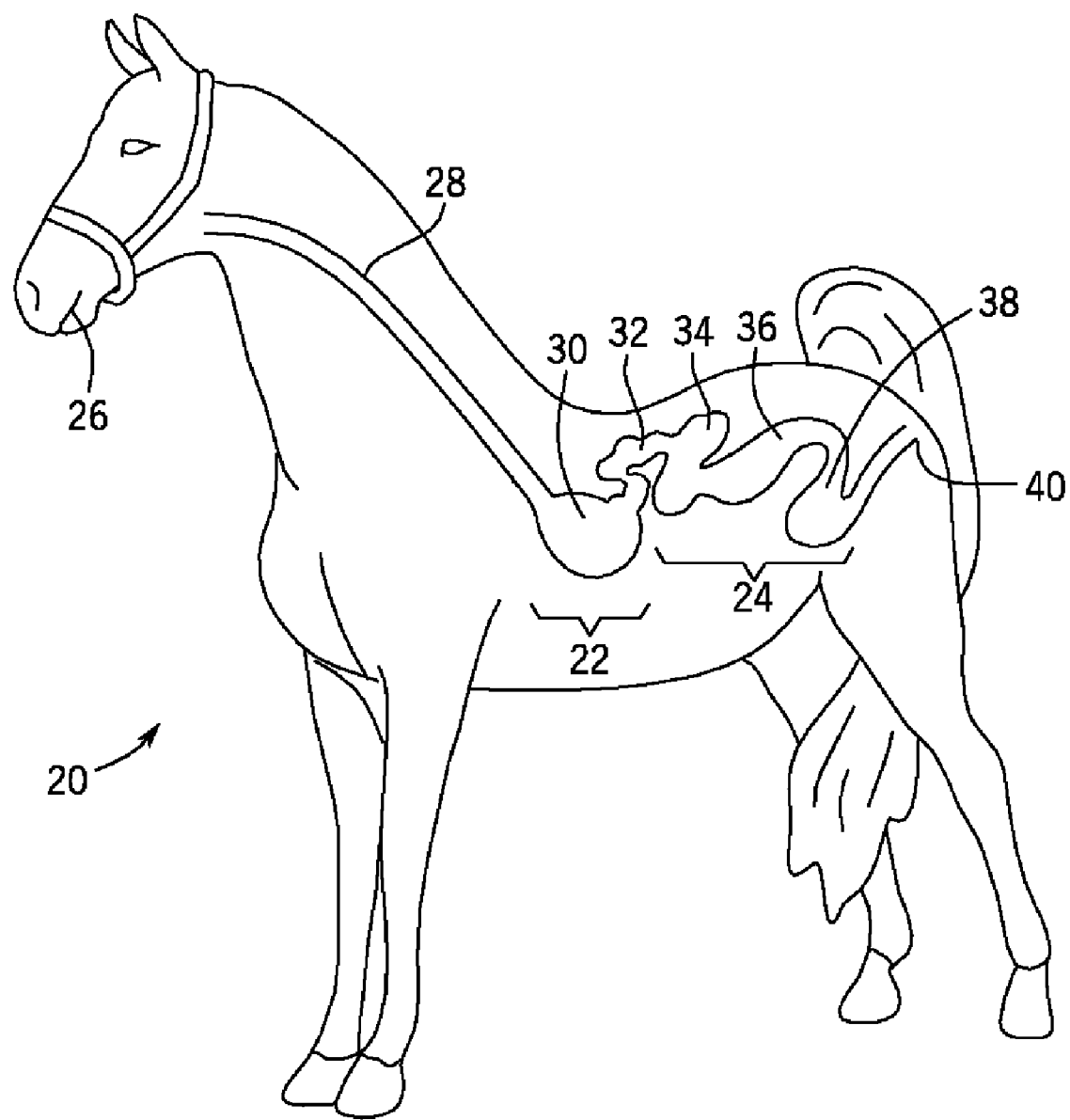
FIG. 1 is a somewhat schematic drawing of a horse showing the anatomy of the horse's digestive tract.

Prior to a discussion of the equine ulcer or bleeding test kit and method of the present invention, it is helpful to briefly discuss the anatomy of the digestive system of a horse. Referring to FIG. 1, a side view of a horse 20 is illustrated, schematically illustrating the digestive tract of the horse. The digestive tract of the horse 20 may be separated into a foregut, which is indicated generally by the reference numeral 22, and a hindgut, which is indicated generally by the reference numeral 24.

The digestive tract of the horse 20 begins at its mouth 26, and sequentially extends through an esophagus 28 into a stomach 30 and then into a small intestine 32, which together constitute the foregut 22 of the horse 20. The foregut 22 of the horse 20 constitutes approximately thirty-five to forty percent of the relative capacity of the digestive tract of the horse 20.

From the small intestine 32, the digestive tract extends through a cecum 34, a large colon 36, and a small colon 38 which terminates in a rectum 40. These elements of the digestive tract of the horse 20 together constitute the hindgut 24 of the horse 20. The hindgut 24 constitutes approximately sixty to sixty-five percent of the relative capacity of the digestive tract of the horse 20.

Figure 2:
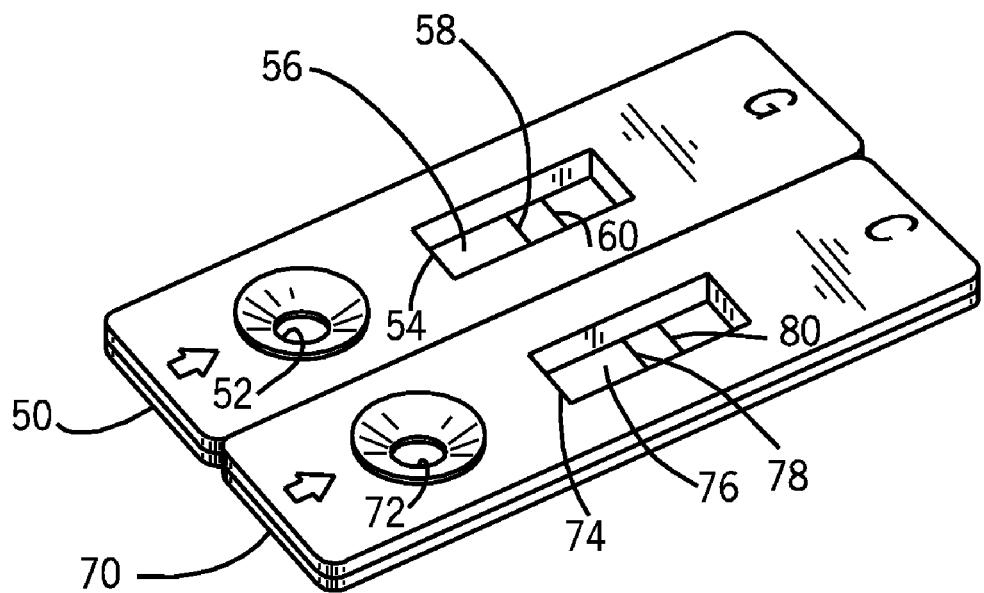
FIG. 2 is an isometric view showing an equine ulcer or bleeding test kit which is constructed and used according to the teachings of the present invention and which has a first casing containing a gastric ulcer or bleeding test strip and a second casing containing a colonic ulcer or bleeding test strip.

The preferred embodiment of the equine ulcer or bleeding test kit of the present invention is shown in FIG. 2. A first casing 50 which contains an equine ulcer or bleeding test kit for detecting gastric ulcers or bleeding is illustrated. The first casing 50 has an aperture 52 located therein into which the fluid to be analyzed will be introduced. Also located in the first casing 50 is a viewing window 54 through which a test strip membrane 56 having a test indicia zone 58 and a control indicia zone 60 located therein is visible. The test indicia zone 58 will become visible when the presence of the substance of interest is detected, thereby providing an indication of the presence of a gastric ulcer or bleeding.

FIG. 2 also shows a second casing 70 which contains an equine ulcer or bleeding test kit for detecting colonic ulcers or bleeding is illustrated. The second casing 70 has an aperture 72 located therein into which the fluid to be analyzed will be introduced. Also located in the second casing 70 is a viewing window 74 through which a test strip membrane 76 having a test indicia zone 78 and a control indicia zone 80 located therein is visible. The test indicia zone 78 will become visible when the presence of the substance of interest is detected, thereby providing an indication of the presence of a colonic ulcer or bleeding. Although they are shown close together, the first casing 50 and the second casing 70 are separate in the embodiment illustrated in FIG. 2.

Figure 3:
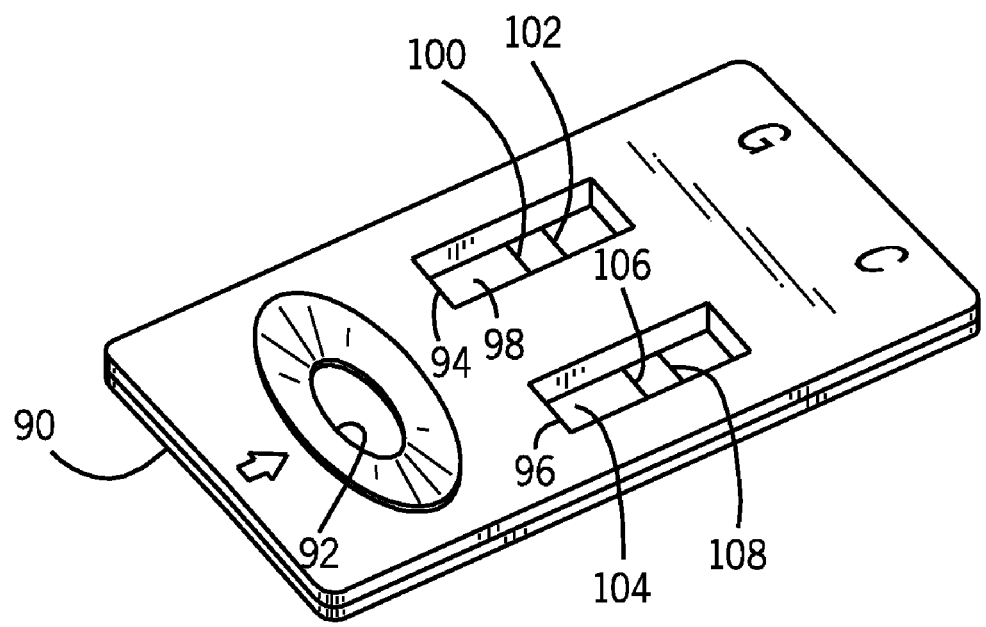
FIG. 3 is an isometric view showing an alternate embodiment equine ulcer or bleeding test kit also constructed and used according to the teachings of the present invention and which has a single casing containing both a gastric ulcer or bleeding test strip and a colonic ulcer or bleeding test strip.

Referring now to FIG. 3, an alternate embodiment test kit is illustrated which has a single casing 90. The casing 90 has a single (but wider) aperture 92 located therein into which the fluid to be analyzed will be introduced. The casing 90 also has first and second viewing windows 94 and 96 located therein on opposite sides thereof. Visible through the first viewing window 94 is a test strip membrane having a test indicia zone 100 and a control indicia zone 102 located therein. The test indicia zone 100 will become visible when the presence of the substance of interest is detected, thereby providing an indication of the presence of a gastric ulcer or bleeding. The control indicia zone 102 will become visible when the sufficient fluid has been introduced into the casing 90 through the aperture 92.

Visible through the second viewing window 96 is a test strip membrane 104 having a test indicia zone 106 and a control indicia zone 108 located therein. The test indicia zone 106 will become visible when the presence of the substance of interest is detected, thereby providing an indication of the presence of a gastric ulcer or bleeding. The control indicia zone 108 will become visible when the sufficient fluid has been introduced into the casing 90 through the aperture 92.

The construction of the test strips 56 and 76 in FIG. 2 and the test strips 98 and 104 in FIG. 3 are well known to those skilled in the art. Similarly, the construction of various other types of test kits having different casing designs are also well known to those skilled in the art. The key portions of the testing devices shown in FIGS. 2 and 3 are the type and derivation of the antibodies which are used to provide the tests for gastric and colonic ulcers or bleeding, which will be discussed below.

Prior to that discussion, a brief description of the operation of the test kits shown in FIGS. 2 and 3 will be provided. A veterinarian, trainer, or horse owner collects a representative fecal sample (ranging from a few grams to an entire bowel movement) from a horse to be tested. The fecal sample is then placed into a container such as a bucket or pail or plastic bag, and an aqueous solution (which may be water or water with a buffer such as salt) is mixed therewith by swirling, stirring, or kneading. Using an eyedropper or any other convenient mechanism, the veterinarian, trainer, or horse owner then places a few drops of the fluid into the test device(s) through the apertures 52 and 72 in the casings 50 and 70, respectively for the embodiment of FIG. 1, or through the aperture 92 in the casing 90 in the embodiment of FIG. 2.

In a few minutes, the control indicia zones 60 and 80 will become visible for the embodiment of FIG. 1, or the control indicia zones 102 and 108 will become visible for the embodiment of FIG. 2, indicating the proper operation of the test kit. If equine albumin is detected, the test indicia zone 58 will become visible for the embodiment of FIG. 1, or the test indicia zone 100 will become visible for the embodiment of FIG. 2. Similarly, if equine hemoglobin is detected, the test indicia zone 78 will become visible for the embodiment of FIG. 1, or the test indicia zone 106 will become visible for the embodiment of FIG. 2. The test thereby diagnoses gastric and/or colonic ulcers or bleeding, providing the basis for immediate treatment if either or both are detected.

While the embodiments illustrated in FIGS. 2 and 3 show separate test strip membranes 56 and 76 for the embodiment illustrated in FIG. 2, and separate test strips 98 and 104 for the embodiment illustrated in FIG. 3, those skilled in the art will immediately appreciate that it is possible to combine both tests on a single membrane. In addition, instead of the test described above wherein the appearance of a test indicia indicates the detection of equine albumin or equine hemoglobin, it is also possible to use the competitive exclusion technique where the appearance of a test indicia indicates the lack of detection of equine albumin or equine hemoglobin.

In the preferred embodiment of the equine ulcer or bleeding test kit and method of the present invention, the substance of interest which, when detected, will provide an indication of the presence of a colonic ulcer or bleeding is equine albumin, and the substance of interest which, when detected, will provide an indication of the presence of a gastric ulcer or bleeding is equine hemoglobin. The choice of equine albumin to indicate the presence of a colonic ulcer or bleeding provides specificity because equine albumin detected in a horse's feces can only have originated from the colon. This is so because blood from gastric ulcers or bleeding (and for that matter any blood cranial to the duodenum) would be degraded by acids and peptidases in the stomach, thereby making it extremely unlikely that equine albumin detected in feces would have originated from a gastric ulcer or bleeding.

However, the action of acids and peptidases in the stomach are unlikely to completely degrade or digest equine hemoglobin. Equine hemoglobin detected in the feces could have originated in the stomach and/or in the colon, thereby indicating either a gastric ulcer or bleeding, a colonic ulcer or bleeding, or both a gastric ulcer or bleeding and a colonic ulcer or bleeding. Differentiation of colonic and gastric ulcers or bleeding is thus reliant on the presence or absence of equine albumin.

Referring to FIG. 4, it may be seen that if equine albumin is detected, a colonic ulcer or bleeding is certainly present. If equine albumin is not detected but equine hemoglobin is detected, a gastric ulcer or bleeding is likely present. If neither equine albumin nor equine hemoglobin is detected, neither gastric ulcers or bleeding nor colonic ulcers or bleeding are likely present. Finally, if both equine albumin and equine hemoglobin are detected, colonic ulcers or bleeding or both gastric ulcers or bleeding and colonic ulcers or bleeding are likely present. Thus, those skilled in the art will appreciate that the equine ulcer or bleeding test kit and method of the present invention thereby provides a mechanism and method for diagnosing gastric and/or colonic ulcers or bleeding, enabling treatment for these ulcers to be provided with confidence.

The Equine Albumin Test

The equine albumin test is a highly sensitive monoclonal/polyclonal immunassay. There are four distinct steps in the creation of such an immunoassay, namely immunization, fusion, cloning, and production. The first stage is immunization, in which a rabbit, mouse, rat, guinea pig, or other suitable test animal is injected with equine albumin peptide sequences derived from the genetic sequence for equine albumin, which is unique to the equine species. This will provoke an immune reaction in the test animal, which will create copious quantities of antibodies in its blood and in its spleen.

At about six weeks, blood may be drawn from the animals and tested for antibodies using an ELISA test. This involves reacting the test animal blood with the horse sera in vitro. If antibodies are present, the ELISA will change color. If an insufficient level of antibodies are present, the test animals may require one or more booster injections of equine albumin. These first bleeds can be used to produce polyclonal antibodies. This stage typically takes approximately three months. Polyclonal antibodies from this stage can be used for test kit construction.

The second stage is fusion, in which the test animals are sacrificed and their spleens are macerated to liberate the cells creating the equine antibodies. These cells may then be fused with a myeloma cell line in order to immortalize them, as described in U.S. Pat. No. 5,552,295, to Stanker et al., which patent is hereby incorporated by reference herein. Once immortalized, these cells can be cultured indefinitely to provide a continuous supply of antibodies.

The hybridomas (fused cells) are then plated out into several ninety-six-well microtiter panels. These cells are challenged with another ELISA test, and those that show the proper antibody reaction may be expanded into additional microtiter wells. These cells are further tested by ELISA testing to provide a pure line of cells producing the desired antibodies, with this stage typically taking approximately five to six weeks.

The third stage is cloning, wherein the cells that tested positive in the second stage are cloned and further tested by ELISA testing. Several cycles of cloning may be required in order to develop stable clones. These clones may then be injected into mice abdomens, where they produce ascites. The monoclonal antibodies are purified from the ascites fluid and are then ready for use. It will be readily apparent to those skilled in the art that this technique will produce novel monoclonal antibodies targeted specifically to equine albumin. The third stage typically takes approximately three months.

Alternatively, chickens may be immunized with the antigen, and will produce antibody in the yolks of their eggs. This technique does not need the cloning stages mentioned above, since the chicken will lay sufficient eggs to provide the antibodies. However, the purification stages of these antibodies are similar to that described above.

The fourth and final stage is the production of test kits. The antibodies are painted onto a porous nitrocellulose or nylon membrane as is conventional in the art. When equine albumin is placed on the test device it is wicked through the membrane, picks up labeled antibodies carrying a coloring agent, and is ultimately trapped by the antibodies in the test indicia zone. There, the concentration of labeled antibodies will cause a color change clearly indicating the presence of equine albumin in the feces of the horse being tested. It will thus be appreciated by those skilled in the art that this novel antibody test is both extremely sensitive (the sensitivity can be as high as approximately one part in one million (one microgram per milliliter)) and specific to equine albumin.

The Equine Hemoglobin Test

The equine hemoglobin test is a highly sensitive monoclonal/polyclonal immunoassay. There are four distinct steps in the creation of such an immunoassay, namely immunization, fusion, cloning, and production. The first stage is immunization, in which a rabbit, mouse, rat, guinea pig, or other suitable test animal is injected with equine hemoglobin peptide sequences derived from the genetic sequence for equine hemoglobin, which is unique to the equine species. This will provoke an immune reaction in the test animal, which will create copious quantities of antibodies in its blood and in its spleen.

At about six weeks, blood may be drawn from the animals and tested for antibodies using an ELISA test. This involves reacting the test animal blood with the horse sera in vitro. If antibodies are present, the ELISA will change color. If an insufficient level of antibodies are present, the test animals may require one or more booster injections of equine hemoglobin. These first bleeds can be used to produce polyclonal antibodies. This stage typically takes approximately three months. Polyclonal antibodies from this stage can be used for test kit construction.

The second stage is fusion, in which the test animals are sacrificed and their spleens are macerated to liberate the cells creating the equine antibodies. These cells may then be fused with a myeloma cell line in order to immortalize them, as described in the Stanker et al. patent referenced above. Once immortalized, these cells can be cultured indefinitely to provide a continuous supply of antibodies.

The hybridomas (fused cells) are then plated out into several ninety-six-well microtiter panels. These cells are challenged with another ELISA test, and those that show the proper antibody reaction may be expanded into additional microtiter wells. These cells are further tested by ELISA testing to provide a pure line of cells producing the desired antibodies, with this stage typically taking approximately five to six weeks.

The third stage is cloning, wherein the cells that tested positive in the second stage are cloned and further tested by ELISA testing. Several cycles of cloning may be required in order to develop stable clones. These clones may then be injected into mice abdomens, where they produce ascites. The monoclonal antibodies are purified from the ascites fluid and are then ready for use. It will be readily apparent to those skilled in the art that this technique will produce novel monoclonal antibodies targeted specifically to equine hemoglobin. The third stage typically takes approximately three months.

Alternatively, chickens may be immunized with the antigen, and will produce antibody in the yolks of their eggs. This technique does not need the cloning stages mentioned above, since the chicken will lay sufficient eggs to provide the antibodies. However, the purification stages of these antibodies are similar to that described above.

The fourth and final stage is the production of test kits. The antibodies are painted onto a porous nitrocellulose or nylon membrane as is conventional in the art. When equine hemoglobin is placed on the test device it is wicked through the membrane, picks up labeled antibodies carrying a coloring agent, and is ultimately trapped by the antibodies in the test indicia zone. There, the concentration of labeled antibodies will cause a color change clearly indicating the presence of equine hemoglobin in the feces of the horse being tested. It will thus be appreciated by those skilled in the art that this novel antibody test is both extremely sensitive (the sensitivity can be as high as approximately one part in one million (one microgram per milliliter)) and specific to equine hemoglobin.

The Combination Test

By combining the equine albumin test with the equine hemoglobin test in a single test kit, a simple, inexpensive, highly sensitive, and diagnosis-specific test for equine ulcers or bleeding may be created. Alternatively, the two tests may be provided in separate test kits. In the preferred embodiment, the two test strips are connected to a single well, so that a single application of the fecal liquid will suffice for both.

If the equine albumin test is positive, a colonic ulcer or bleeding is indicated. If only the equine hemoglobin test is positive, a gastric ulcer or bleeding is indicated. If both results are positive, then either a colonic ulcer or bleeding or both a gastric ulcer or bleeding and a colonic ulcer or bleeding is indicated. It will be appreciated by those skilled in the art that this dual test can provide a convenient, non-invasive test for gastric ulcers or bleeding (which are currently difficult and expensive to diagnose) as well as colonic ulcers or bleeding (for which no current test capable of providing an accurate diagnosis exists).

Although the equine ulcer or bleeding test kit and method of the present invention are in the preferred embodiment targeted at the diagnosis of both gastric ulcers or bleeding and colonic ulcers or bleeding in horses, it is contemplated and within the scope of the present invention that it may be used for the diagnosis of gastric ulcers or bleeding and colonic ulcers or bleeding in other animals as well. The particular ulcer or bleeding test kit may be designed specifically for the particular animal with which it will be used to detect albumin and hemoglobin of the particular animal. Alternately, a more generic animal gastric ulcers or bleeding and colonic ulcers or bleeding test kit may be made by providing an albumin antibody which specifically binds to albumin of a plurality of different animals and a hemoglobin antibody which specifically binds to hemoglobin of a plurality of different animals.

It may therefore be appreciated from the above detailed description of the preferred embodiment of the present invention that it teaches an equine ulcer and digestive tract bleeding test kit and a related method for the use of the test kit which are efficacious in the diagnosis of both gastric ulcers or bleeding and colonic ulcers or bleeding in horses. The equine ulcer or bleeding test kit and method of the present invention provide a highly specific indication as to the presence of either gastric ulcers or bleeding or colonic ulcers or bleeding, or both. The equine ulcer or bleeding test kit and method of the present invention are highly reliable both in their identification of the existence of ulcers or bleeding in a horse as well as their identification of the type(s) of the ulcers or the location of the bleeding which are present in the horse, and do not produce excessive false positive readings.

The equine ulcer or bleeding test kit and method of the present invention are both simple and quick to perform, and they require no special skill or training in order for a user to perform the test. The equine ulcer or bleeding test kit of the present invention is entirely self-contained, and requires no laboratory analysis or additional processing equipment, thereby enabling it to be performed anywhere as a field test. The equine ulcer or bleeding test kit and method of the present invention provide the results of the test quickly, in minutes rather than requiring an extended time.

The equine ulcer or bleeding test kit of the present invention is of a construction which is both durable and long lasting, and the test kits do not require special storage conditions and have an extended shelf life. The equine ulcer or bleeding test kit of the present invention is also of inexpensive construction to enhance its market appeal and to thereby afford it the broadest possible market. Finally, all of the aforesaid advantages and objectives of the equine ulcer or bleeding test kit and method of the present invention are achieved without incurring any substantial relative disadvantage.

Although the foregoing description of the equine ulcer or bleeding test kit of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. A rapid test kit for the detection and localization of digestive tract bleeding in equines that may be indicative of ulcers, comprising:

a first test strip for a rapid immunoassay or peroxidase reaction to detect a first substance indicative of the presence of gastric bleeding and/or colonic bleeding in an equine that may in turn be indicative of the existence of a gastric ulcer and/or a colonic ulcer in the equine; and a second test strip for a rapid immunoassay to detect a second substance different from said first substance which second substance is indicative of the presence of colonic bleeding in an equine that may in turn be indicative of the existence of a colonic ulcer in the equine.

2. The rapid test kit as defined in claim 1, wherein said first substance detected by said first test strip comprises equine hemoglobin.

3. The rapid test kit as defined in claim 2 wherein said first test strip contains an anti-equine hemoglobin antibody which specifically binds to equine hemoglobin.

4. The rapid test kit as defined in claim 3, wherein said anti-equine hemoglobin antibody binds equine hemoglobin with a sensitivity equal to or better than approximately one part in one million (one microgram per milliliter).

5. The rapid test kit as defined in claim 3, wherein said anti-equine hemoglobin antibody is a monoclonal antibody.

6. The rapid test kit as defined in claim 3, wherein said anti-equine hemoglobin antibody is a polyclonal antibody.

7. The rapid test kit as defined in claim 3, wherein said anti-equine hemoglobin antibody is isolated from the blood serum or the macerated spleens of inoculated rabbits, mice, rats, or guinea pigs.

8. The rapid test kit as defined in claim 3, wherein said anti-equine hemoglobin antibody is produced by a hybridoma cell line which produces and secretes monoclonal antibodies which specifically bind to equine hemoglobin.

9. The rapid test kit as defined in claim 3, wherein said anti-equine hemoglobin antibody is produced by expressing equine hemoglobin antibodies from immune cells which have been hybridized with immortal myeloma lines.

10. The rapid test kit as defined in claim 9, wherein said immune cells are isolated from the blood serum or the macerated spleens of inoculated rabbits, mice, rats, or guinea pigs.

11. The rapid test kit as defined in claim 1, wherein said first test strip also contains a control indicator to demonstrate that the test has been properly performed.

12. The rapid test kit as defined in claim 1, wherein said first substance detected by said second test strip comprises equine albumin.

13. The rapid test kit as defined in claim 1, wherein said second test strip contains an anti-equine albumin antibody which specifically binds to equine albumin.

14. The rapid test kit as defined in claim 13, wherein said anti-equine albumin antibody binds equine albumin with a sensitivity equal to or better than approximately one part in one million (one microgram per milliliter).

15. The rapid test kit as defined in claim 13, wherein said anti-equine albumin antibody is a monoclonal antibody.

16. The rapid test kit as defined in claim 13, wherein said anti-equine albumin antibody is a polyclonal antibody.

17. The rapid test kit as defined in claim 13, wherein said anti-equine albumin antibody is isolated from the blood serum or the macerated spleens of inoculated rabbits, mice, rats, or guinea pigs.

18. The rapid test kit as defined in claim 13, wherein said anti-equine albumin antibody is produced by a hybridoma cell line which produces and secretes monoclonal antibodies which specifically bind to equine albumin.

19. The rapid test kit as defined in claim 13, wherein said anti-equine albumin antibody is produced by expressing equine albumin antibodies from immune cells which have been hybridized with immortal myeloma lines.

20. The rapid test kit as defined in claim 19, wherein said immune cells are isolated from the blood serum or the macerated spleens of inoculated rabbits, mice, rats, or guinea pigs.

21. The rapid test kit as defined in claim 1, wherein said second test strip contains a control indicator to demonstrate that the test has been properly performed.

22. The rapid test kit as defined in claim 1, wherein said first and second test strips comprise:

a single test strip for detecting both the presence of equine hemoglobin which is indicative of the presence of gastric bleeding and/or colonic bleeding in an equine that may in turn be indicative of the existence of a gastric ulcer and/or a colonic ulcer in the equine and the presence of equine albumin which is indicative of the presence of colonic bleeding in an equine that may in turn be indicative of the existence of a colonic ulcer in the equine.

\* \* \* \* \*

UNITED STATES PATENT AND TRADEMARK OFFICE
CERTIFICATE OF CORRECTION

| | |
|---|---|
| PATENT NO. | : 8,168,446 B2 |
| APPLICATION NO. | : 12/619459 |
| DATED | : May 1, 2012 |
| INVENTOR(S) | : Franklin L. Pellegrini and Scott D. Carter |

Page 1 of 1

It is certified that error appears in the above-identified patent and that said Letters Patent is hereby corrected as shown below:

In the specification:

Column 7, line 63:

"window 94 is a test strip membrane having a test indicia zone" should read --window 94 is a test strip membrane 98 having a test indicia zone--.

Signed and Sealed this

Nineteenth Day of June, 2012

David J. Kappos
*Director of the United States Patent and Trademark Office*